United States Patent [19]

Thiesse et al.

[11] Patent Number: 5,807,584
[45] Date of Patent: Sep. 15, 1998

[54] VANILLIN AND/OR ETHYLVANILLIN SOLID BEADS

[75] Inventors: Jean-Claude Le Thiesse, Saint-Etienne; Eraclis Statiotis, Villette D'Anthon; Jean Brossette, Meyzieu, all of France

[73] Assignee: Rhone-Poulenc Chimie, Courbevoie Cedex, France

[21] Appl. No.: 496,611

[22] Filed: Jun. 29, 1995

[30] Foreign Application Priority Data

Jun. 29, 1994 [FR] France ................................. 94 07994

[51] Int. Cl.$^6$ ..................................................... A61K 9/16
[52] U.S. Cl. .......................... 424/489; 426/516; 514/951; 264/5; 264/13
[58] Field of Search ........................... 424/489; 426/516; 514/951

[56] References Cited

U.S. PATENT DOCUMENTS 5,225,227  7/1993  Yalpani ................................. 426/580

OTHER PUBLICATIONS

Database WPI—Week 8838, Derwent Publication Ltd., London, GB; AN 88–266465 & JP–A–63 097 168 (Nippon Oil Seal Ind.) Apr. 27, 1988.

*Primary Examiner*—James M. Spear
*Attorney, Agent, or Firm*—Burns, Doane, Swecker & Mathis, L.L.P.

[57] ABSTRACT

Storage-stable, free-flowing and attrition-resistant, essentially spheroidal solid beads of vanillin and/or ethylvanillin, characteristically prilled from a melt thereof, are useful flavoring/perfuming agents.

19 Claims, 3 Drawing Sheets

VANILLIN AND/OR ETHYLVANILLIN SOLID BEADS

BACKGROUND OF THE INVENTION

1. Technical Field of the Invention:

The present invention relates to morphologically improved vanillin and/or ethylvanillin particulates, and, more especially, to vanillin and/or ethylvanillin beads and to a process for the preparation thereof.

2. Description of the Prior Art:

Vanillin is a known material which is widely used in numerous fields or industries as a flavoring agent or perfume.

Vanillin is thus widely used in the food industry, but it also has applications in other fields, such as pharmacy or perfumery. It is consumed in vast amounts.

Vanillin is currently commercially available in the form of a crystalline powder. This presents the drawback of producing fine particles which present the disadvantages of dusting and poor flowability during storage and manipulation or handling of the powder. In addition, clogging can also occur during prolonged storage.

SUMMARY OF THE INVENTION

Accordingly, a major object of the present invention is the provision of an improved morphological form of vanillin and/or ethylvanillin which avoids, or conspicuously ameliorates, the above disadvantages and drawbacks to date characterizing the state of this art.

Briefly, the present invention features storage-stable, free-flowing and attrition-resistant, essentially spheroidal solid beads of vanillin and/or ethylvanillin.

DETAILED DESCRIPTION OF BEST MODE AND PREFERRED EMBODIMENTS OF THE INVENTION

More particularly according to the present invention, by the terms "vanillin" and "ethylvanillin" are also intended the respective isomers thereof, isovanillin and isoethylvanillin.

By the term "beads" are intended solid, highly spherical particulates.

According to the present invention, vanillin and/or ethylvanillin beads are prepared by melting the vanillin and/or ethylvanillin, if necessary, then fragmenting the molten mass into droplets and solidifying the droplets thus produced in a gaseous cooling stream such that the droplets solidify into beads, which are then recovered.

In a preferred embodiment of the invention, the vanillin and/or ethylvanillin is melted, then the molten mass is injected through a nozzle to form droplets, and the droplets are solidified by free-falling through a tower against a countercurrent stream of a cold gas and then recovered.

The beads produced in accordance with the invention have unique physico/chemical properties.

The definitions and the techniques used to determine these properties are more fully described below.

The vanillin and/or ethylvanillin beads are in the form of white spherules. They are essentially spherical in shape having a diameter which can vary over a wide range. Thus, the particle size of the beads advantageously ranges from 200 $\mu$m to 3,000 $\mu$m, preferably from 300 $\mu$m to 1,000 $\mu$m. The particle size is determined by screening through metal sieves.

Generally, the particle size, expressed as the median diameter ($d_{50}$), ranges from 500 $\mu$m to 2,000 $\mu$m, preferably from 500 $\mu$m to 1,000 $\mu$m. The median diameter is defined as that at which 50% by weight of the particles have a diameter which is greater or lesser than the median diameter.

Figure 1:
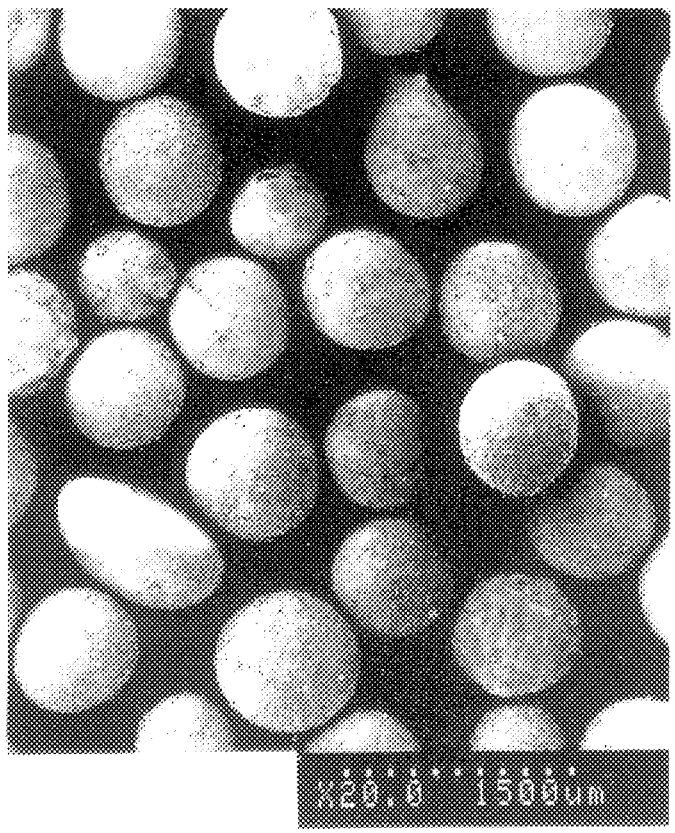
FIG. 1 and FIG. 2 are scanning electron photomicrographs showing the morphology of solid vanillin beads according to the present invention.
Figure 2:
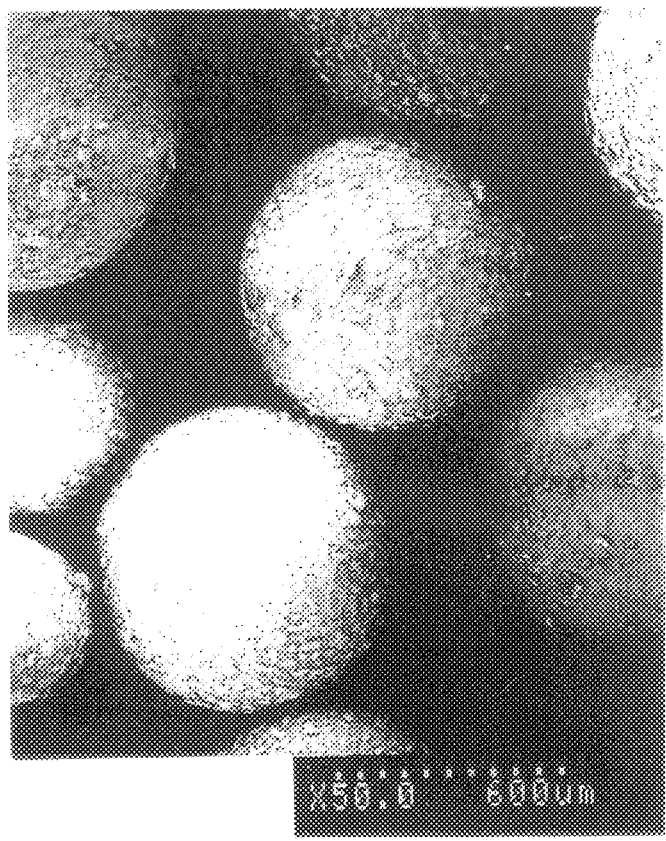

FIGS. 1 and 2 are scanning electron photomicrographs (with respective magnifications of 20× and 50×) which show the morphology of the vanillin beads in accordance with the invention. A uniform granulometric distribution (monodispersity) can be seen in the product.

The density of the beads can be high or low. The bulk density (loose packed) of the beads is preferably at least 0.7, and more preferably ranges from 0.7 to 0.9. It will be appreciated that the beads of the invention have a much higher density than that of the crystalline powder.

The physical form of the vanillin and/or ethylvanillin beads of the invention indicates they are resistant to attrition.

The cohesion of the subject beads indicates that they have good flow properties or characteristics.

Their discharge coefficient is thus substantially improved over that of crystalline powder, as will be seen in the examples to follow.

The instantaneous discharge coefficient is always much higher than 10, and possibly infinity.

The novel morphology of the products of the invention is a result of the process for the preparation thereof.

The process of the invention for the preparation of the vanillin and/or ethylvanillin beads comprises melting vanillin and/or ethylvanillin, then fragmenting the molten mass into droplets and solidifying the droplets obtained in a gaseous cooling current, such that the droplets solidify into beads which are then recovered.

The process of the invention uses molten vanillin and/or ethylvanillin.

The molten vanillin and/or ethylvanillin can be supplied directly from a production line.

It is also possible to first melt the vanillin and/or ethylvanillin if it is provided in powder form. The product is heated to its melting point. Preferably, the product is heated to a temperature which is slightly higher than the melting point, preferably at most 5° C. above the melting point. For vanillin, this temperature ranges from 81° C. to 86° C. For ethylvanillin, this temperature ranges from 74° C. to 79° C.

It is possible to use vanillin with added ethylvanillin, and vice versa. Preferably, less than 40%, more preferably less than 20%, of the other constituent is employed. The temperature to which the mixture must be heated to melt it can be readily determined by one skilled in this art, via simple techniques.

The addition of soluble additives or fine suspensions of additives to the vanillin and/or ethylvanillin is also within the scope of the invention.

The melting operation is generally carried out with stirring. In a preferred embodiment of the invention, this operation is carried out in an inert gas atmosphere, possibly a noble gas, but preferably nitrogen, for economic reasons.

In a subsequent step, the molten mass is transformed into droplets. This operation can be carried out using any fragmentation means, for example injection through a flat nozzle having circular orifice(s).

In one preferred embodiment of the invention, the droplets are formed by injecting the molten mass through an orifice, in particular through a nozzle.

The subsequent operation then ensures solidification of the droplets into beads, by contact with a cold gas at a temperature of from −50° C. to 0° C., preferably from −30° C. to −10° C.

The cold gas can be any gas provided that it is inert vis-a-vis vanillin and/or ethylvanillin. Preferably, nitrogen or oxygen-depleted air (for example to 10%) is used.

The cold gas current is preferably countercurrent to the flow of the beads.

The residence time, i.e., the period between droplet formation at the outlet of the nozzle and its arrival in the recovery system, advantageously ranges from 1 to 10 seconds, preferably from 3 to 5 seconds.

One technique for obtaining the desired residence time is to permit the droplets to fall in a tower countercurrently to a cold gas, as described above.

Finally, the beads are recovered via any known means, for example under gravity in a recovery tank, or by fluidized bed technique.

With respect to the apparatus used to carry out the process of the invention, this includes two assemblies: a first assembly for forming the beads and a second assembly for recovering the beads.

The first assembly comprises a storage tank, which is preferably stirred when the vanillin and/or ethylvanillin emanates from a production line, or a melter to melt the vanillin and/or ethylvanillin, and a vessel which is typically a tower comprising means for fragmentation of the melt into droplets at its upper end, preferably a nozzle, and having one or more inlets for a cold gas in the lower end, which transforms the base of the tower into a cooling tower.

The height of the tower can vary widely, for example from 6 to 40 meters, depending on the size of the installation. It should be appreciated that the upper limit is not critical.

The vanillin and/or ethylvanillin is introduced via a double-screw hopper into a melter which is a reactor provided with a system for regulating the temperature, for example a double envelope, to maintain the vanillin and/or ethylvanillin in the molten state.

The nozzle can have a single orifice or it can be a multi-orifice nozzle having from 1 to 3,000 orifices, preferably between 1 and 100 holes.

A system comprising a plurality of nozzles, for example two nozzles, preferably moveable and in parallel, can be employed.

The diameter of the orifices in the nozzle depends on the desired bead size. It can range from 50 to 2,000 μm, but it preferably ranges from 200 μm to 600 μm.

The orifice size is always smaller than the size of the bead produced. Thus, a nozzle with orifices of about 200 μm is used to prepare beads having a median diameter of 500 μm.

The nozzle can be a static nozzle, but can also be a nozzle provided with a high frequency electrical vibration system, for example from 100 to 10,000 hertz. This apparatus produces droplets having perfectly calibrated sizes.

The molten mass is preferably delivered at the nozzle at an overpressure provided by a gaseous current, preferably a nitrogen current. The overpressure with respect to the atmospheric pressure is preferably 5% to 500%.

The nozzle temperature is maintained at the melting point of the product.

It is possible, but not essential, to provide a gas current at the level of the nozzle, preferably a cocurrent of nitrogen with the jet exiting the nozzle. This gas current is preferably at a temperature which is between room temperature and 80° C. The presence of this gaseous cocurrent produces improved regularity in the dimensions of the beads and prevents coalescence of the droplets.

Baffles and screens can be provided in the upper end of the tower to distribute the gas stream homogeneously.

A cold gas current, preferably nitrogen or oxygen-depleted air, is introduced at the base of the tower. This cold gas stream solidifies the droplets into beads. Its temperature preferably ranges from −50° C. to 0° C., more preferably from −30° C. to −10° C.

The cold gas current preferably exits the tower below the nozzle, at a distance of about one-tenth of the total height of the cooling zone.

The bead recovery system at the base of the tower is not critical. It may comprise a recovery tank, or a means for fluidizing the particle bed. It is constituted by a tank, preferably cylindrical, comprising a screen in its lower end through which a gaseous current is flowed, preferably nitrogen or oxygen-depleted air. The gas flow rate, which depends on the particle size, must be such that the particles are maintained fluidized. For a fluid bed diameter of 80 mm, for example, the flow rate may range from 5 to 30 m³/h.

The cooling may be continued in this region of the apparatus.

The fluidization apparatus contains an outlet for evacuation of the beads.

Figure 3:
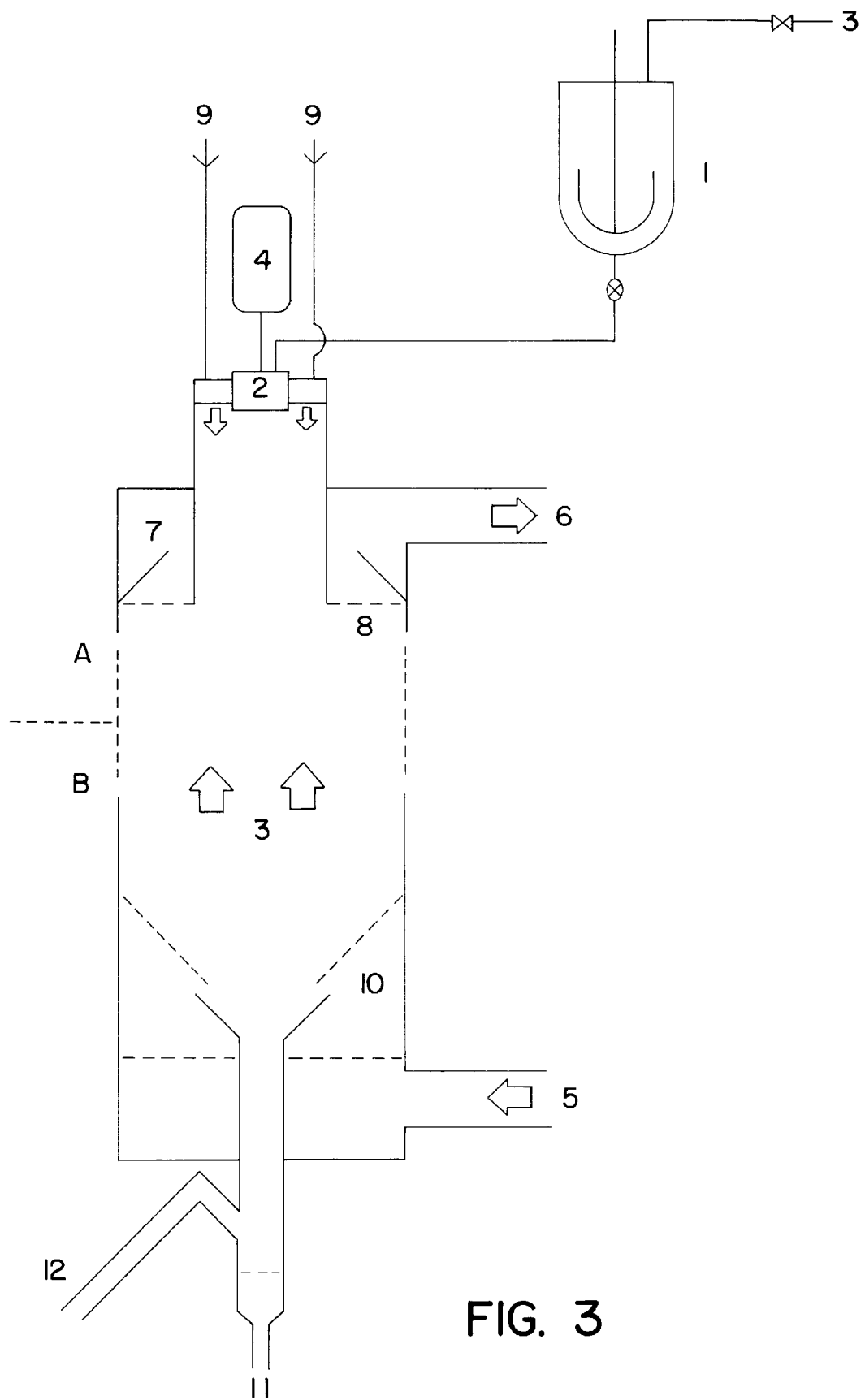
FIG. 3 is a schematic side view of one type of apparatus for preparing solid vanillin/ethylvanillin beads according to this invention.

One embodiment of the process/apparatus of the invention is illustrated in FIG. 3 of the accompanying drawings.

FIG. 3 is a schematic side view of an apparatus for carrying out the process of the invention.

The apparatus comprises two sections: the upper section or prilling tower A and the lower section which comprises a fluidization chamber B.

Vanillin (and/or ethylvanillin) powder is introduced into vessel 1 where it is melted before being directed to nozzle 2. This is carried out by introducing nitrogen via line 3 at an overpressure into the storage tank 1.

The tower is 8 meters high and its upper end includes a nozzle 2 which is integral with a vibrator 4. Its lower end is provided with an inlet 5 for a current of cold oxygen-depleted air.

The cooling air introduced at 5 exits the tower via outlet 6 disposed below nozzle 2.

The upper end of the tower is provided with baffles 7 and an annular screen 8 which homogeneously distributes the gas stream in the tower. A warm nitrogen stream, at a temperature of from 20° C. to 80° C., preferably from 60° C. to 80° C., is distributed via line 9 as a cocurrent around the nozzle 2.

The lower end of the tower has a conical section screen 10 for guiding the solidified beads into a fluidization chamber comprising a nitrogen inlet 11 and an outlet 12 for continuous removal of the beads produced.

In order to further illustrate the present invention and the advantages thereof, the following specific examples are given, it being understood that same are intended only as illustrative and in nowise limitative.

Figure 4:
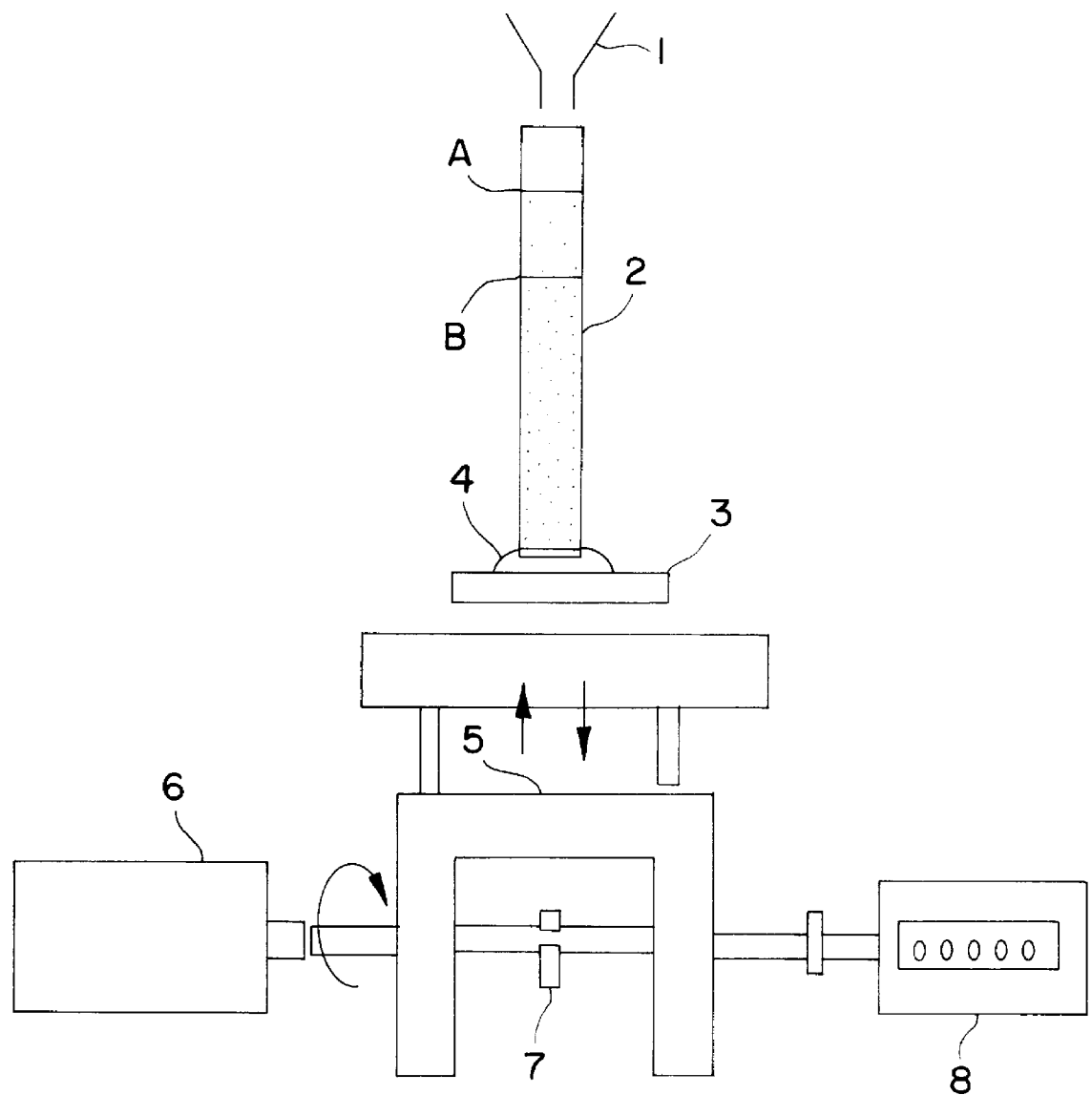
FIG. 4 is a schematic front view of an apparatus for measuring the bulk density of the solid vanillin/ethylvanillin beads according to this invention.

In said examples to follow, the techniques employed to determine the different characteristics of the final products were:

Packed and loose packed bulk density:

This was measured using the apparatus illustrated in FIG. 4.

First, the empty sample holder 2 was weighed.

The powder to be measured was introduced into sample holder 2 by means of funnel 1 until the height of the bed of powder reached the 250 cm$^3$ mark on the graduated sample holder (level A).

The weight of the powder was determined by weighing the full sample holder.

The sample holder was fixed to the support 3 by clips 4.

The counter 8, which counts the number of strikes made on the base of the sample holder, was set to zero.

The sample holder was subjected to vertical shocks applied to its base by hammer 5 driven by motor 6 via a cam 7. The operation was ceased when the volume obtained was constant (level B).

The evolution of the bulk volume indicated on the graduations on the sample holder was recorded as a function of the shocks applied by the hammer.

An experimental packing curve was obtained.

Bulk volume=f(number of shocks) which was transformed into a curve of bulk density=f(number of shocks).

The bulk density was determined according to the relationship:

$$\text{bulk density} = \frac{\text{mass of powder introduced (g)}}{\text{bulk volume (cm}^3\text{)}}$$

Discharge coefficient:

The flow properties of the products of the invention were measured in a Jenike cell using the method described by L. Svarosvsky in *Powder Testing Guide: Methods of measuring the physical properties of bulk powders,* Elsevier Applied Science pp 49–52 (1987).

It will be appreciated that a powder having a higher discharge coefficient flows more easily and that a powder is considered to be very cohesive when it has a discharge coefficient of 2, and much less if it has a discharge coefficient of less than 4. A powder is considered to flow well with a discharge coefficient of more than 4.

Dissolution rate in various media:

x g of beads were introduced into one liter of a liquid, described below, in a test tube at 25° C., with stirring (200 revolutions per minute).

The evolution of UV absorbence in the solution was monitored (spectrophotometer) as a function of time. The dissolution time, expressed in seconds, was obtained when the absorbence stabilized at its final value.

In the examples to follow, the vanillin beads were prepared in an apparatus as shown in FIG. 3.

The nozzle, which was vibrated, had the characteristics reported in the examples below.

500 g of crystalline vanillin were used.

The vanillin powder was introduced into vessel 1. The nitrogen overpressure at 3 varied depending on the particular example; it was close to 0.1 bar.

The vanillin was melted by means of hot water circulating in the double envelope. The product temperature was 84° C. in vessel 1 and the temperature at the nozzle outlet 2 is reported in the Table for each example. The flow rate of the product at the nozzle outlet 2 is also reported in each Table.

Cooling air was introduced via line 5 at a flow rate of 850 m$^3$/h, providing a speed in the tower of 0.6 m/s. The air exited via outlet 6.

The following temperatures are also reported in each Table:
  (i) temperature of the air at tower inlet 5,
  (ii) temperature of the air at the tower outlet 6,
  (iii) temperature of the fluidization air at 11.

The beads were collected at 10 and recovered at 12.

EXAMPLE 1

Vanillin beads were prepared in an apparatus as shown in FIG. 3, comprising a nozzle with a single orifice, the orifice diameter being 400 µm. The ratio L/D was 3; L is the length of the orifice and D is the diameter of the orifice.

The process was carried out as described above. The operating conditions were as reported in Table I below:

TABLE I

| | |
|---|---|
| Vibration frequency of nozzle 2, in hertz | 1,020 |
| Nitrogen overpressure 3, bars | 0.10 |
| Temperature of molten product at 2, in °C. | 83.5 |
| Flow rate of product at nozzle 2 outlet, in kg/h | 0.95 |
| Temperature of air at tower inlet 5, in °C. | −30 |
| Temperature of air at tower outlet 6, in °C. | −20 |
| Temperature of air of fluidized bed 11, in °C. | −35 |

After 31 minutes of operation, 500 g of beads were recovered having a median diameter ($d_{50}$) of 900 µm.

EXAMPLE 2

Vanillin beads were prepared in an apparatus as shown in FIG. 3, comprising a nozzle with a single orifice, the orifice diameter being 250 µm. The ratio L/D was 3; L is the length of the orifice and D is the diameter of the orifice.

The process was carried out as described above. The operating conditions were as reported in Table II below:

TABLE II

| | |
|---|---|
| Vibration frequency of nozzle 2, in hertz | 2,000 |
| Nitrogen overpressure 3, bars | 0.15 |
| Temperature of molten product at 2, in °C. | 81.5 |
| Flow rate of product at nozzle 2 outlet, in kg/h | 0.46 |
| Temperature of air at tower inlet 5, in °C. | −35 |
| Temperature of air at tower outlet 6, in °C. | −25 |
| Temperature of air of fluidized bed 11, in °C. | −55 |

500 g of beads were recovered having a median diameter ($d_{50}$) of 500 µm.

EXAMPLE 3

Vanillin beads were prepared in an apparatus as shown in FIG. 3, comprising a nozzle with a single orifice, the orifice diameter being 250 µm. The ratio L/D was 3; L is the length of the orifice and D is the diameter of the orifice.

The process was carried out as described above. The operating conditions were as reported in Table III below:

TABLE III

| | |
|---|---|
| Vibration frequency of nozzle 2, in hertz | 848 |
| Nitrogen overpressure 3, bars | 0.14 |
| Temperature of molten product at 2, in °C. | 81.5 |
| Flow rate of product at nozzle 2 outlet, in kg/h | 0.43 |
| Temperature of air at tower inlet 5, in °C. | −10 |
| Temperature of air at tower outlet 6, in °C. | −5 |
| Temperature of air of fluidized bed 11, in °C. | −55 |

500 g of beads were recovered having a median diameter ($d_{50}$) of 640 μm.

EXAMPLE 4

Vanillin beads were prepared in an apparatus as shown in FIG. 3, comprising a nozzle with a single orifice, the orifice diameter being 200 μm. The ratio L/D was 3; L is the length of the orifice and D is the diameter of the orifice.

The process was carried out as described above. The operating conditions were as reported in Table IV below:

TABLE IV

| | |
|---|---|
| Vibration frequency of nozzle 2, in hertz | 1,520 |
| Nitrogen overpressure 3, bars | 0.17 |
| Temperature of molten product at 2, in °C. | 82 |
| Flow rate of product at nozzle 2 outlet, in kg/h | 0.27 |
| Temperature of air at tower inlet 5, in °C. | −20 |
| Temperature of air at tower outlet 6, in °C. | −15 |
| Temperature of air of fluidized bed 11, in °C. | −55 |

500 g of beads were recovered having a median diameter ($d_{50}$) of 520 μm.

EXAMPLE 5

1. Vanillin beads were prepared in an apparatus as shown in FIG. 3, comprising a nozzle with seven orifices, each orifice having a diameter of 350 μm. The ratio L/D was 5; L is the length of the orifice and D is the diameter of the orifice.

The process was carried out as described above. The operating conditions were as reported in Table V below:

TABLE V

| | |
|---|---|
| Vibration frequency of nozzle 2, in hertz | 966 |
| Nitrogen overpressure 3, bars | 0.17 |
| Temperature of molten product at 2, in °C. | 83 |
| Flow rate of product at nozzle 2 outlet, in kg/h | 4.8 |
| Temperature of air at tower inlet 5, in °C. | −50 |
| Temperature of air at tower outlet 6, in °C. | −30 |
| Temperature of air of fluidized bed 11, in °C. | −30 |

After 30 minutes of operation, 2,400 g of beads were recovered having a median diameter ($d_{50}$) of 710 μm.

2. The physico/chemical characteristics of the beads obtained were as follows:

The loose packed bulk density was 0.78 and the packed bulk density was 0.81.

The discharge coefficient, measured in a Jenike cell, was infinite, and the instantaneous discharge coefficient was 3 after 1 day of storage with consolidation. By way of comparison, the values were 3 and 0.6, respectively, for a commercial powdered crystalline vanillin.

The dissolution rates in different media, measured according to the technique described above, are reported in Table VI:

TABLE VI

| Quantity of beads introduced (g) | Dissolution medium at 25° C. | Bead dissolution time | | | |
|---|---|---|---|---|---|
| | | 50% by wt | 80% by wt | 90% by wt | 100% by wt |
| 0.5 | aqueous sucrose solution, 10% by wt | 45 s | 1 min, 10 s | 1 min, 30 s | 4 min |
| 0.5 | aqueous solution, pH = 2 acidified with HCl | 1 min | 1 min, 30 s | 2 min | 3 min, 30 s |
| 200 | monopropyleneglycol | 2 min | 4 min | 6 min | 10 min |
| 200 | ethanol | | | | 2 min |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Storage-stable, free-flowing and attrition-resistant solid beads consisting essentially of vanillin and/or ethylvanillin.

2. Storage-stable, free-flowing and attrition-resistant solid beads comprising vanillin and/or ethylvanillin and having a particle size ranging from greater than 200 μm to 3,000 μm.

3. The solid beads as defined by claim 2, having a particle size ranging from 300 μm to 1,000 μm.

4. The solid beads as defined by claim 1, having a median diameter ranging from 500 μm to 2,000 μm.

5. The solid beads as defined by claim 4, having a median diameter ranging from 500 μm to 1,000 μm.

6. Storage-stable, free-flowing and attrition-resistant solid beads comprising vanillin and/or ethylvanillin and having a loosely packed bulk density of at least 0.7.

7. The solid beads as defined by claim 6, having a loosely packed bulk density ranging from 0.7 to 0.9.

8. Storage-stable, free-flowing and attrition-resistant solid beads comprising vanillin and/or ethylvanillin and having an instantaneous discharge coefficient greater than 10.

9. The solid beads as defined by claim 1, consisting essentially of vanillin.

10. The solid beads as defined by claim 1, consisting essentially of ethylvanillin.

11. A process for the preparation of the solid beads as defined by claim 1, comprising prilling droplets of a melt of vanillin and/or ethylvanillin into a feedstream of a coolant gas, thereby solidifying said droplets into beads, and thence recovering the beads thus produced.

12. The process as defined by claim 11, said coolant gas flowing countercurrently to said molten droplets.

13. The process as defined by claim 11, said molten droplets having a temperature at most 5° above the melting point thereof.

14. The process as defined by claim 11, comprising prilling said droplets through a single-orifice or multi-orifice nozzle.

15. The process as defined by claim 14, the orifice(s) of said nozzle having a diameter ranging from 50 µm to 2,000 µm.

16. The process as defined by claim 14, said nozzle comprising a high frequency electrical vibrator.

17. The process as defined by claim 11, comprising solidifying said droplets into beads in from 1 to 10 seconds.

18. Storage-stable, free-flowing and attrition-resistant solid beads comprising 20% or more vanillin and/or ethylvanillin.

19. The solid beads according to claim 18, comprising 40% or more vanillin or ethylvanillin.

* * * * *